United States Patent [19]
Soll et al.

[11] Patent Number: 5,673,153
[45] Date of Patent: Sep. 30, 1997

[54] VIEWING ASSEMBLY FOR PRODUCING AN OPTICALLY CORRECTED REFLECTED IMAGE

[75] Inventors: David B. Soll, Rydal, Pa.; Richard Evans Feinbloom, New York, N.Y.

[73] Assignee: Image Optical Corporation, Wilmington, Del.

[21] Appl. No.: 542,771

[22] Filed: Oct. 13, 1995

Related U.S. Application Data

[63] Continuation of Ser. No. 116,169, Sep. 2, 1993, Pat. No. 5,497,274.

[51] Int. Cl.[6] ............................................ G02B 5/08
[52] U.S. Cl. .......................... 359/846; 359/847; 359/849; 359/868
[58] Field of Search ....................... 359/838, 846, 359/847, 848, 849, 868, 869, 870, 863, 862, 883, 900; 40/900; 472/63; 132/316

[56] References Cited

U.S. PATENT DOCUMENTS

| | | | |
|---|---|---|---|
| 1,685,032 | 9/1928 | Parsons | 359/849 |
| 2,579,225 | 12/1951 | Borst et al. | 359/849 |
| 2,733,637 | 2/1956 | Joseph | 88/96 |
| 3,004,472 | 10/1961 | Buxton | 359/846 |
| 3,374,047 | 3/1968 | Gatchell | 350/199 |
| 3,539,247 | 11/1970 | Broussard | 359/847 |
| 3,552,835 | 1/1971 | Benzies | 359/847 |
| 3,610,738 | 10/1971 | Bochmann | 359/847 |
| 3,623,793 | 11/1971 | Merten et al. | 359/847 |
| 3,623,796 | 11/1971 | Schweiger | 359/847 |
| 3,628,852 | 12/1971 | Snaper et al. | 359/849 |
| 3,677,620 | 7/1972 | Bettencourt | 359/817 |
| 3,733,116 | 5/1973 | Hutchinson | 359/847 |
| 3,776,637 | 12/1973 | Hecht | 359/868 |
| 3,781,095 | 12/1973 | Rushing et al. | 359/847 |
| 3,827,782 | 8/1974 | Boudouris et al. | 359/846 |
| 3,832,039 | 8/1974 | Doolittle | 359/846 |
| 3,893,755 | 7/1975 | Cobarg et al. | 359/847 |
| 3,970,369 | 7/1976 | Wachsman | 359/732 |
| 3,972,600 | 8/1976 | Cobarg | 359/847 |
| 3,996,947 | 12/1976 | Szpur et al. | 132/316 |
| 4,056,309 | 11/1977 | Harbison et al. | 359/847 |
| 4,119,366 | 10/1978 | Lemaitre | 359/847 |
| 4,128,310 | 12/1978 | Miller | 359/847 |
| 4,226,507 | 10/1980 | Fuschetto | 359/849 |
| 4,243,301 | 1/1981 | Powell | 359/847 |
| 4,261,655 | 4/1981 | Honigsbaum | 351/41 |
| 4,266,857 | 5/1981 | Svenson | 359/849 |
| 4,418,990 | 12/1983 | Gerber | 351/41 |
| 4,734,557 | 3/1988 | Alfille et al. | 359/847 |
| 4,913,536 | 4/1990 | Barnea | 359/666 |

FOREIGN PATENT DOCUMENTS

| | | | |
|---|---|---|---|
| 1475736 | 2/1967 | France | 359/849 |
| 2379078 | 8/1978 | France | 359/846 |
| 2255789 | 5/1974 | Germany | 132/316 |
| 2261679 | 6/1974 | Germany | 132/316 |
| 283136 | 11/1934 | Italy | 359/846 |
| 52-76046 | 6/1977 | Japan | 359/849 |
| 61-198207 | 9/1986 | Japan | 359/846 |
| 1418636 | 8/1988 | U.S.S.R. | 359/846 |
| 2152701 | 8/1985 | United Kingdom | 359/868 |

OTHER PUBLICATIONS

Hardy, J.W., "Active Optics: A New Technology for the Control of Light", *Proceedings Of The IEEE*, vol. 66, No. 6, Jun. 1978, 651–697.

*Primary Examiner*—Paul M. Dzierzynski
*Assistant Examiner*—John Juba, Jr.
*Attorney, Agent, or Firm*—Panitch Schwarze Jacobs & Nadel, P.C.

[57] ABSTRACT

The present invention is a viewing assembly that can selectively create optical compound corrections in the images reflected from the viewing assembly. The viewing assembly includes a reflective surface coupled to a supporting body in such a manner that the reflective surface conforms to the contour of the supporting body. The contour of the supporting body can then be selectively altered by the viewer of the viewing assembly, thereby changing the shape of the reflective surface and creating desired optical corrections in the viewed reflected images.

23 Claims, 9 Drawing Sheets

VIEWING ASSEMBLY FOR PRODUCING AN OPTICALLY CORRECTED REFLECTED IMAGE

This is a continuation of application Ser. No. 08/116,169, filed Sep. 2, 1993, now U.S. Pat. No. 5,497,274.

FIELD OF THE INVENTION

The present invention relates to a viewing assembly that corrects a reflected image in such manner so as to compensate for an imperfection in the viewer's eyesight and, more particularly, to such viewing assemblies that can selectively provide optical corrections to a reflected image corresponding to the needs of the viewer.

BACKGROUND OF THE INVENTION

Many people have imperfect vision that requires correction through the use of prescriptive lenses. However, it is not always desirable or practical to use prescriptive lenses when performing certain tasks that require accurate vision. For example, when a person views himself or herself in a mirror for the purpose of shaving, applying cosmetics, or the like, clear vision is obviously desired. However, the use of eyeglasses in such situations is impractical because conventional eyeglasses obstruct the person's face. Another situation where wearing prescriptive lenses is impractical, is when a person is selecting spectacle frames to support their prescriptive lenses. In such a situation, the person selecting the spectacle frames cannot clearly view his or her image in a plano or flat mirror unless the needed prescriptive lenses are held in front of the frames being sampled. This, however, obstructs part of the reflective image the person is trying to view.

Mirrors are optical devices that reflect light, in accordance with the contours of their reflective surfaces. As such, mirrors can be formed with varied focal points so as to compensate for any one person's visual imperfections. However, most every person's visual impairments differ from those of other persons. Therefore, it is impossible to form a single fixed mirror surface that can compensate for the visual imperfections of all, or even most, people. As such, mirrors have been invented that have variable focal lengths in an attempt to allow each person to adjust the mirror to best correct his or her own vision.

Some of the simplest ways to produce a variable mirror focal point is to place a corrective lens in front of a fixed flat mirror. The corrective lens may include custom formed lenses or the corrective lens may be adjustably positioned relative to the flat mirror, thereby allowing the focal length of the mirror to be altered. The prior art of such corrective lens mirrors is exemplified in U.S. Pat. Nos. 3,374,047 to Gatchell; 3,677,620 to Bettencourt and 3,970,369 to Wachsman. As can be recognized by a person skilled in the art, the variability of such corrective lens mirrors is limited by the optical characteristics of the corrective lens being used. Therefore, one mirror cannot be created for use by all people regardless of their visual impairment.

A second prior art method of varying the focal length of a mirror is accomplished by selectively varying the contour of the mirror surface. In such systems, the mirror surface is formed on a flexible backing, thereby allowing the mirror surface to be flexed into a convex or concave orientation. In some systems, such as U.S. Pat. No. 2,733,637 to Joseph, the mirror surface is flexed by compressing the frame of the mirror. Another common means of deforming the mirror is through the use of pneumatics or hydraulics, creating a fluid pressure on one side of the mirror that causes it to deform. Such pneumatic or hydraulic mirror systems are exemplified in U.S. Pat. Nos. 3,623,793 to Mertem; 3,632,796 to Schweiger; 3,972,600 to Cobary; 4,119,366 to LeMaitre; 4,128,310 to Miller and 4,913,536 to Barnea. Additionally, the deformation of optical elements using a pneumatic means have also been used in applications other than that of corrective mirrors. For example, in U.S. Pat. No. 4,261,655 to Honigsbaum, there is shown a pneumatic method used to shape prescriptive lenses within a pair of eyeglasses.

The problem inherent in the pneumatically or hydraulically deformed mirrors of the prior art is that the pressure used to deform the mirror surface, produces only a spherical concave or convex correction to the reflected image. However, many people who wear glasses have corrective lenses that create cylindrical or torical corrections in a viewed image. The conventional prior art systems are incapable of producing cylindrical or torical corrections in the reflected image, therefore limiting the ability of prior art mirror systems to accurately compensate for prescriptive lenses.

It is therefore a primary objective of the present invention to provide a viewing assembly that reflects an image that can be adjustably corrected spherically, cylindrically and/or torically, thereby allowing the present invention viewing assembly to correct a reflected image in a more accurate manner.

SUMMARY OF THE INVENTION

Briefly stated, the present invention comprises an adjustable reflective surface which has an adjustment mechanism coupled to it. The adjustment mechanism varies a degree of curvature of the reflective surface to selectively create a toric correction in the reflective surface. The toric correction enables a visually impaired user to view an image on the reflective surface without the use of a corrective lens.

In another aspect, the invention comprises a viewing apparatus having a formable body. A plurality of flexible members are disposed within the formable body, each of the plurality of flexible members is configured to have a predetermined curvature within the formable body. A force adjustment device selectively applies a force to one or more of the plurality of flexible members and alters the predetermined curvature of one or more of the plurality of flexible members, causing the formable body to selectively change shape. A reflective surface is coupled to the formable body. The reflective surface changes in shape with the formable body and produces an optical correction in a reflected image viewed from the reflective surface.

In another aspect, the invention comprises a viewing apparatus which has a flexible material with a front surface and a back surface. The front surface is reflective. A support structure has a first surface which receives the back surface of the flexible material in corresponding facing engagement. The first surface has a contour. A tensioning device pulls the flexible material taut over the first surface of the support structure and the flexible material conforms to the contour of the first surface.

In yet another aspect, the invention comprises a method of creating optical corrections in a viewing assembly which comprises the steps of coupling a reflective surface to a supporting body which has a contour. The reflective surface conforms to the contour of the supporting body and selectively alters the contour of the supporting body, thereby altering the reflective surface and producing the optical corrections in an image reflected from the reflective surface.

BRIEF DESCRIPTION OF THE DRAWINGS

For a better understanding of the present invention, reference is made to the following descriptions of exemplary embodiments thereof, considered in conjunction with the accompanying drawings, in which.

DETAILED DESCRIPTION OF THE PREFERRED EMBODIMENTS

Each person's eyesight is unique to that person, and for that reason eyeglasses are produced by prescription for the specific visual imperfections of an individual. The strength of individual lenses is dependent upon the index of refraction for the material of the lens, the thickness of the lens and the surface curvatures of the lens surfaces. The material, thickness and curvature characteristics of a set of lenses are then matched with the needs of an individual, to produce the needed visual corrections.

In producing corrective lenses for eyesight, there are three primary surface shapes into which the surface of a corrective lens is usually formed. The first surface is a spherical surface. A spherical surface is that found along the surface of a ball, wherein all points on the spherical surface share a common radius to a single common point. Therefore, the radius of curvature for a spherical surface is constant across the entire spherical surface.

In many applications, corrective lenses are needed with a surface curvature that is not spherical. Therefore, a lens surface can be formed into the shape of a cylindrical surface. A cylindrical curvature is that found on a surface of a cylinder. A cylindrical surface has a single radius of curvature as measured at a perpendicular from the longitudinal axis of the cylinder. However, the longitudinal axis of the cylinder is not curved. As such, a cylindrical surface has a meridian that has substantially no optical power. The meridian of no optical power is conventionally known as the axis of the cylindrical surface.

The third type of surface shape, into which a corrective lens can be formed, is a toric surface. A toric surface is a combination of a spherical surface with a cylindrical surface. As such, in a toric surface, the curvature of the surface along each meridian is different and no meridian lacks optical power. In modern corrective lenses, toric surfaces are used more commonly than are cylindrical surfaces or spherical surfaces alone.

As will be recognized by a person skilled in the art, the curvature of a lens surface is referred to as a diopter. A diopter is a measure of the power of a lens equal to the reciprocal of its focal length in meters. For instance, a one diopter lens has a focal length of one meter. The ordinary range of toric lens curvatures, including practically all commonly used lens surfaces, spans from plus or minus zero to twenty diopters of spherical power to four cylindrical diopters in one quarter diopter steps. Additionally, diopter values are usually denoted as being either negative (−) or positive (+), so as to denote the curvature of a concave surface or convex surface, respectively.

Figure 1:
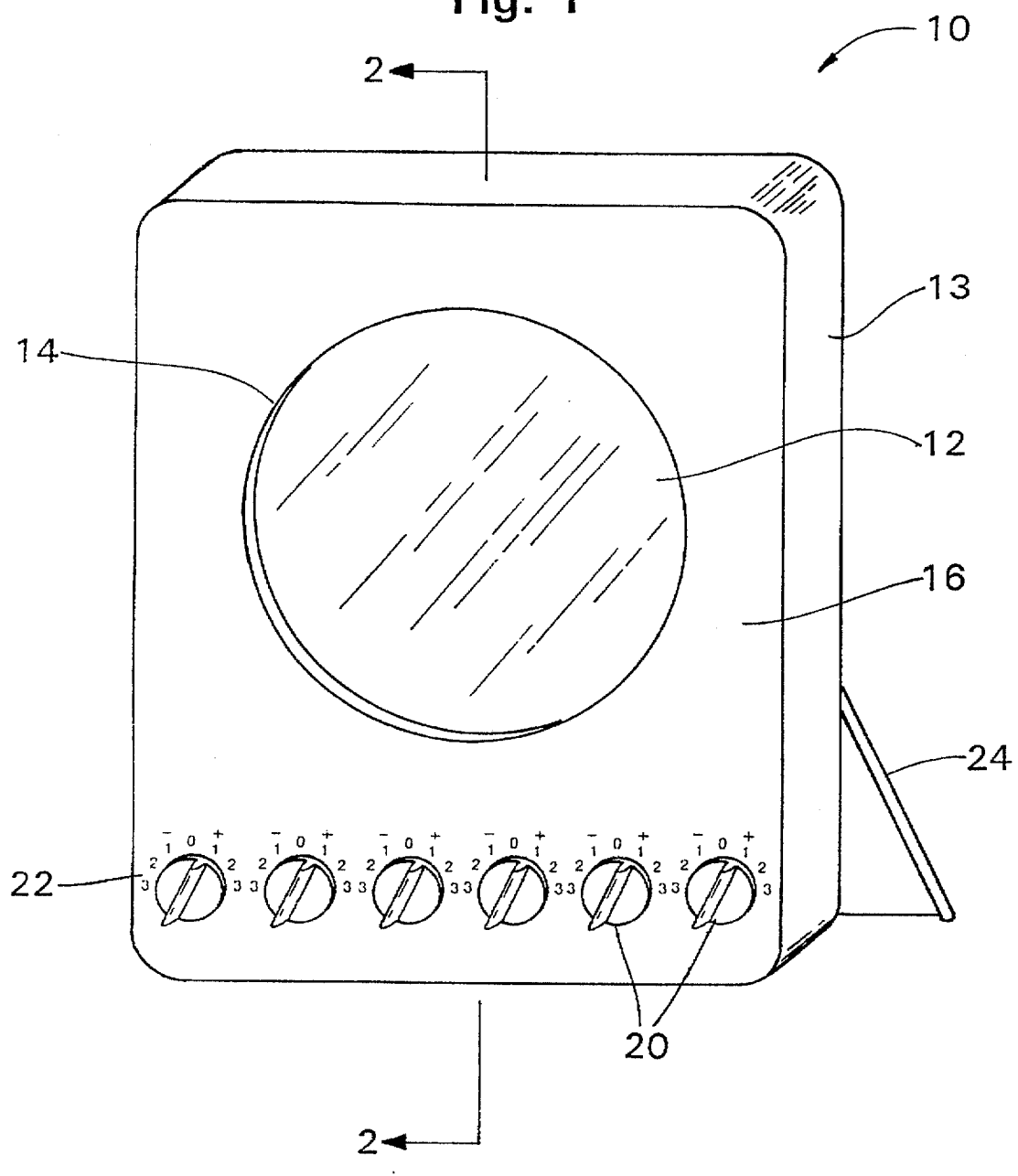
FIG. 1 is a perspective view of one preferred embodiment of the present invention viewing assembly.

Referring to FIG. 1, an embodiment of the present invention viewing assembly 10 is shown having a reflective surface 12 positioned within a housing 13. A view window 14 is formed through the face surface 16 of the housing 13 so that a person viewing the face surface 16 of the housing 13 can see the reflective surface 12. A plurality of adjustment knobs 20 are positioned below the view window 14 on the face surface 16 of the housing 13. As will be later explained, the adjustment knobs 20 control the curvature of the reflective surface 12, thereby enabling the curvature of the reflective surface 12 to be selectively adjusted as desired. Reference numerals 22 or other indicia are disposed around each of the adjustment knobs 20 to provide a reference as to the rotational position of each of the adjustment knobs 20. As will be later explained, the reference numerals 22 can be used to apply a desired curvature to the reflective surface 12 that corresponds to a specific eyeglass prescription. The viewing assembly 10 may include a support stand member 24 or similar device used to support the viewing assembly 10 upright at a desired angle of inclination. It is understood by those skilled in the art that the present invention is not limited to counter top or desk top use. That is, the viewing assembly 10 could be sized as a full length mirror to allow a person to view their entire body without the use of corrective lenses.

Figure 2:
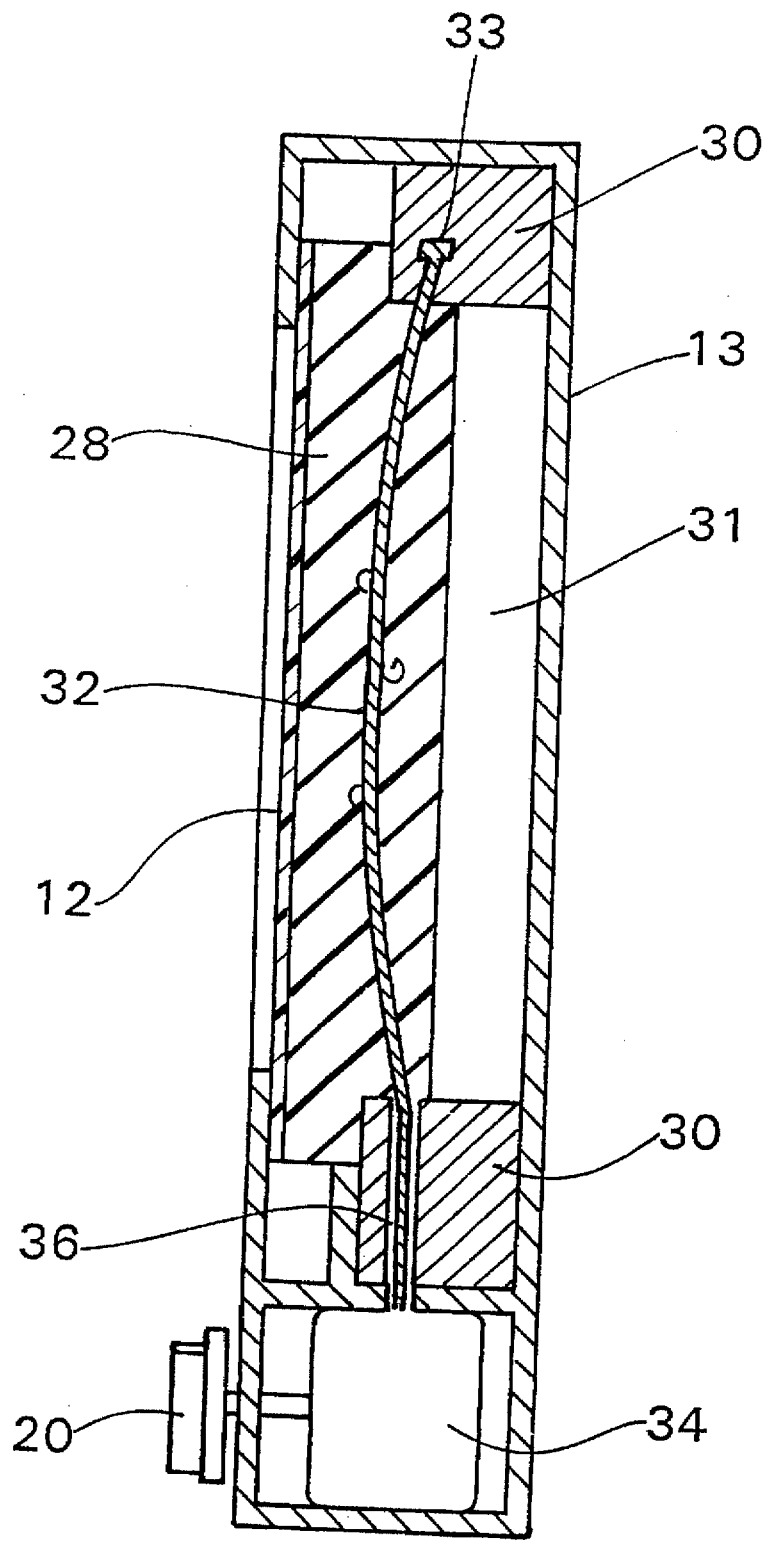
FIG. 2 is a cross-sectional view of the embodiment of the present invention shown in FIG. 1, viewed along section line 2—2.

Referring to FIG. 2, it can be seen that the reflective surface 12 is disposed upon a flexible or formable body 28 (hereinafter "flexible body 28"). In the present embodiment, it is preferred that the body 28 be formed of an elastomeric material, such as silicone or GERTV. However, it is understood by those skilled in the art that the body 28 could be constructed of other flexible or formable materials, such as isoprene rubbers, natural rubbers, CIS polyisoprene rubbers, neoprene rubbers, butyl rubbers, nitrile copolymers, silicone, hypalon, acrylic, thiokol or polyurethane. The flexible body 28 is seated within a rigid frame structure 30 inside the housing 13. The rigid frame structure 30 surrounds an open central region 31. The flexible body 28 is shaped to abut against one side of the rigid frame structure 30 and partially extend into the open central region 31. Although the rigid frame structure 30 is shown as a separate element, it should be understood that the rigid frame structure 30 can be unistructurally formed as part of the mirror housing 13.

In the present embodiment, it is preferred that the reflective surface 12 be constructed of a flexible mirror material, such as a thin metal coated polymer. Examples of the metal coated polymers include aluminized polyesters or MYLAR®. It is understood by those skilled in the art that other flexible reflective materials could be used without departing from the spirit and scope of the invention. The reflective surface 12 is preferably bonded to the flexible body 28 by a suitable bonding process within the knowledge of those skilled in the art.

The flexible body 28 is mechanically joined to the rigid frame structure 30 by a plurality of flexible generally elongate members 32. In the shown embodiment, each flexible member 32 has one end 33 that is anchored to the rigid frame structure 30. Each of the flexible members 32 extends through the flexible body 28, following a predetermined curvature. Each flexible member 32 exits the flexible body 28 and enters a conduit 36 in the rigid frame structure 30 at a point opposite its anchored end 33. The flexible members 32 pass through the conduits 36 and are each coupled to a tensioning mechanism 34 below the rigid frame structure 30. The tensioning mechanisms 34 are controlled by the adjustment knobs 20 that extend through the housing 13. The tensioning mechanisms 34 can be any known assembly capable of advancing the flexible members 32 into, and retracting the flexible members 32 from, the conduits 36 in the rigid frame structure 30, such as a spool (not shown) secured to an adjustment knob. The passage of the flexible members 32 within various conduits 36, prevents the bending or buckling of the flexible members 32 within the rigid frame structure 30, as the flexible members 32 are selectively advanced by the tensioning mechanisms 34. As will be later explained, by selectively adjusting the tensioning mechanisms 34, the curvature of the flexible member 32 within the flexible body 28 can be changed, resulting in a change in the shape of a flexible body 28 and a corresponding change in the curvature of the reflective surface 12.

Figure 3:
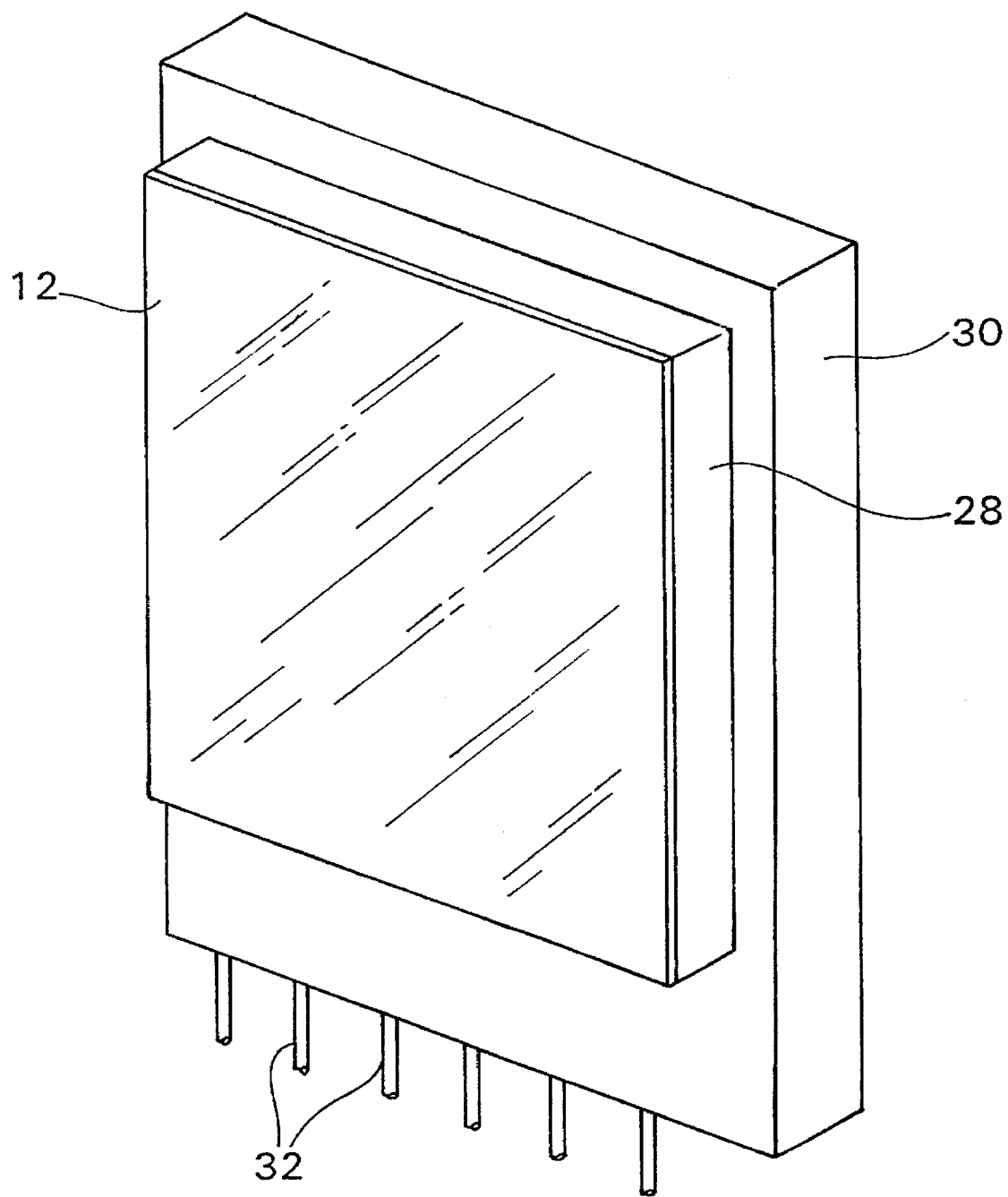
FIG. 3 is an isolated perspective view of the reflective surface, of the present invention viewing assembly, disposed upon an elastomeric body and held within a rigid frame structure in accordance with a preferred construction of the present invention.

In FIG. 3, there is shown an isolated view of the flexible body 28 and reflective surface 12, seated within the rigid frame structure 30. As can be seen, the flexible body 28 abuts one side of the rigid frame structure 30 and covers the area of the open center region 31 (shown in FIG. 2). The flexible body 28 fills at least part of the open center region 31 such that the flexible members 32 extend through the flexible body 28 as the flexible members 32 pass across the open center region 31 within the rigid frame structure 30.

Figure 4:
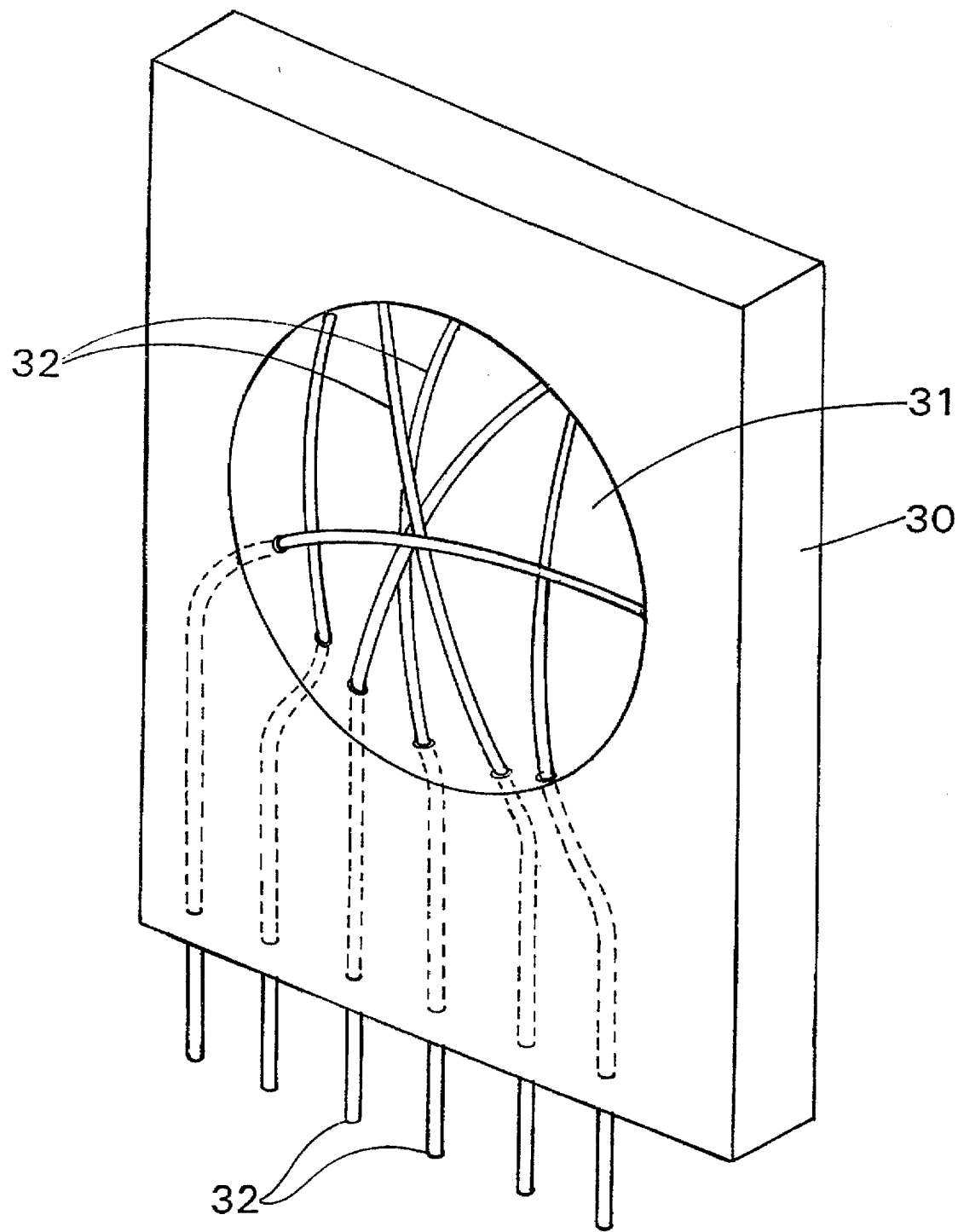
FIG. 4 is an isolated perspective view of the rigid frame structure of the present invention viewing assembly, shown without the presence of the elastomeric body to facilitate discussion and consideration.

Referring to FIG. 4, the rigid frame structure 30 and flexible members 32 are shown without the reflective surface 12 or the material of the flexible body 28, as was previously shown in FIG. 3. As can now be seen, the flexible members 32 traverse the open center region 31 of the rigid frame structure 30 at a plurality of orientations. In the shown embodiment, there are six flexible members 32, however, it should be understood that any plurality can be used. The flexible members 32 can be made of any strong flexible material, such as wire or flat strapping, so long as the flexible members 32 bend when compressed and become linear when made taut. In the present embodiment, the wires are preferably constructed of music wire and have a diameter equal to approximately 0.035 inches. The various flexible members 32 can be arranged in any orientation, wherein the flexible members 32 may lay in parallel rows so as to create an overall cylindrical shape, or may crisscross cross each other's path, to create an overall spherical shape. Regardless of the selected orientations of the flexible members 32, each of the flexible members 32 is initially compressed to bow outwardly along a predetermined curved path as the flexible members 32 cross the open center region 31. However, the curved path followed by each of the flexible members 32 need not be the same. Each of the flexible members 32 is initially oriented to follow a desired spherical cylindrical curvature which produces a toric curve that spans the open center region 31. Although the curvature of each of the flexible members 32 can be the same, in a preferred embodiment, one, or any plurality of flexible members 32, may follow a spherical curvature while the other flexible members 32 follow a cylindrical curvature. If some of the flexible members 32 follow spherical curves and others follow cylindrical curves, the combination of the flexible members 32 creates an overall toric surface across the open center region 31. The initial curvatures of each of the flexible members 32 are preserved in a first position as the material of the flexible body 28 (shown in FIG. 3) is molded around the flexible members 32 within the open center region 31. Consequently, each of the flexible members 32 is enveloped by the flexible body 28 and each of the flexible members 32 retains its initial curvature by the presence of the material of the flexible body 28 surrounding each flexible member 32.

Figure 5A:
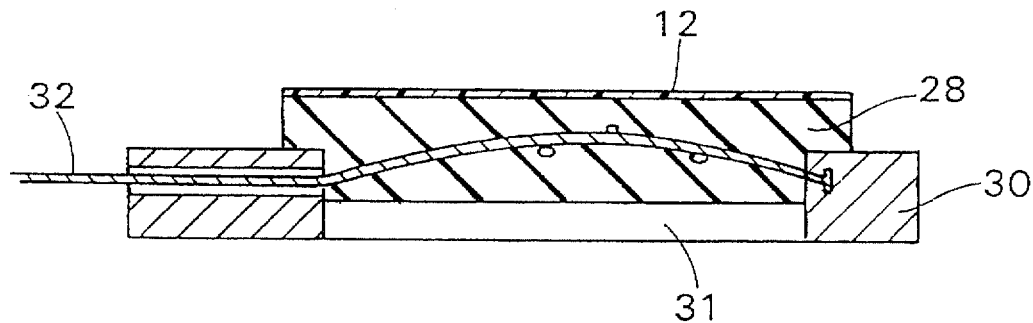
FIGS. 5a, 5b and 5c are isolated cross-sectional views of the reflective surface and supporting elastomeric body, of the present invention viewing assembly, selectively formed into three separate curvatures so as to facilitate consideration and discussion of the operation of the present invention.

Referring to FIG. 5a, a cross section of the flexible body 28 seated within the rigid frame structure 30 is shown. When the flexible members 32 are in the first position each flexible member 32 follows its initial spherical or cylindrical curvature within the material of the flexible body 28. The flexible body 28 is shaped so that the reflective surface 12 lays in a flat plane when the flexible members 32 are in the first position. However, when the tensioning mechanisms (shown in FIG. 2) are manipulated to advance one or more flexible members 32 toward the flexible body 28, the effected flexible members 32 bend outwardly, and change from the initial curvature of the first position to a more curved orientation.

Figure 5B:
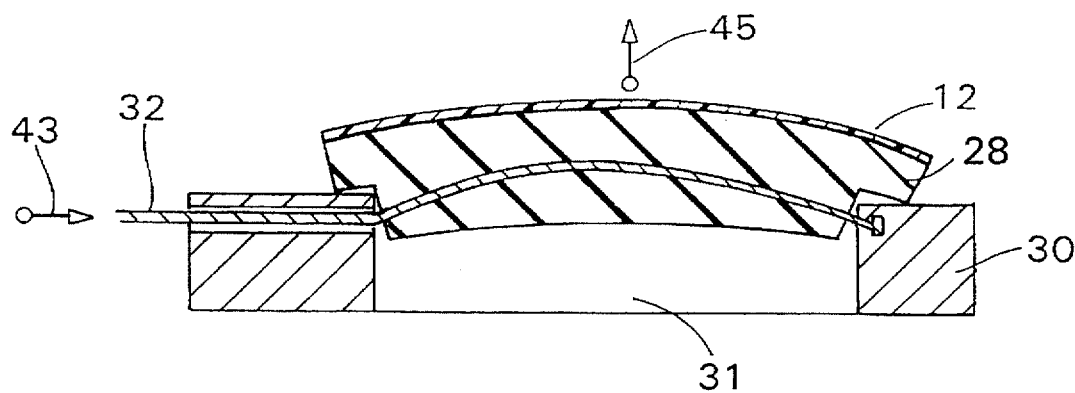

Referring to FIG. 5b, it can be seen that as a flexible member 32 is increasingly advanced in the direction of arrow 43, the curvature of the flexible member 32 changes. Each flexible member 32 bows in an even manner, creating a semicircular path from one end of the open center region 31, to the other. The more a flexible member 32 is advanced, the smaller the radius of curvature for a semicircular path becomes. Since each flexible member 32 is enveloped by the material of the flexible body 28, the bending of the flexible members 32 causes the flexible body 28 to deform outwardly in the direction of arrow 45. The resulting deformation of the flexible body 28 causes the reflective surface 12 to deform, thereby altering the reflective characteristics of the reflective surface 12. Each of the flexible members 32 extends across the open center region 31 and passes through the flexible body 28 along a different line. Some of the flexible members 32 cross over the middle of the open center region 31 while other flexible members 32 only extend across a small segment of the open center region 31. Consequently, as each of the flexible members 32 is advanced by the tensioning mechanism, the change in curvature in each of the flexible members 32 creates a distinct change in curvature to the portion of the flexible body 28 near which that particular flexible member 32 passes. In the shown embodiment, there are six flexible members 32, as such the deformation of the flexible body 28 can be controlled by applying a tension or compression force, in any possible combination, to the six flexible members 32. As a result, the flexible body 28 can be adjusted along six different meridians, thereby allowing the reflective surface to be selectively adjustable along six separate meridians. Consequently, most any spherical or cylindrical curvatures can be created to produce a desired toric curve in the flexible body 28, wherein the toric curve is transferred to the reflective surface 12.

Figure 5C:
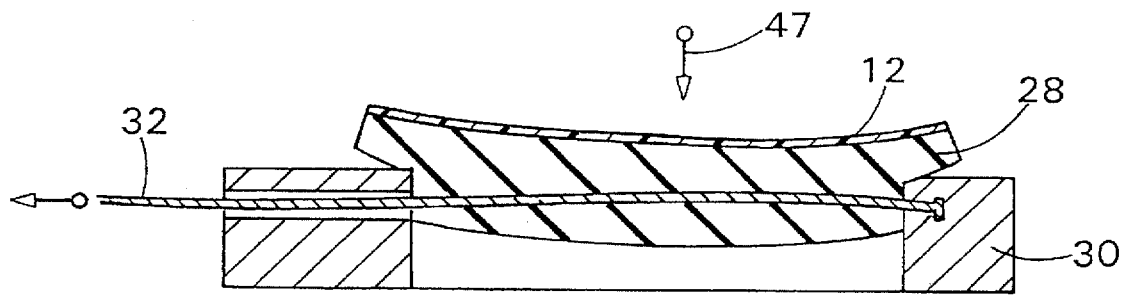

Furthermore, if the tensioning mechanisms or force adjustment devices (shown in FIG. 2) are manipulated to apply tension to one or more of the flexible members 32, the effected flexible members 32 change to a less curved orientation. Referring to FIG. 5c, it can be seen that as a flexible member 32 is increasingly made taut, the curvature of the flexible member 32 becomes less pronounced. The straightening of the flexible members 32 also causes the flexible body 28 to deform inwardly in the direction of arrow 47. The resulting deformation of the flexible body 28 is transferred to the reflective surface 12. Consequently, by adding the ability of making the flexible members 32 taut, the range of adjustments for the reflective surface is increased and the reflective surface 12 can be selectively adjusted to optically correct a larger range of eyesight imperfections.

While in the present embodiment it is preferred that the flexible members 32 have an initial curvature when the reflective surface 12 lies generally in a flat plane (as shown in FIG. 5a), it is understood by those skilled in the art that the particular initial orientation of the flexible members 32 with respect to the shape of the reflective surface 12 could be different. For instance, the flexible members 32 could lie in a generally flat plane when the reflective surface 12 is positioned in a generally flat plane such that the flexible members 32 and reflective surface 12 extend generally parallel with respect to each other, initially. The flexible members 32 could then be deformed upwardly to cause the reflective surface 12 to deform as shown in FIG. 5b. Similarly, the flexible members 32 could be flexed downwardly to cause the reflective surface 12 to deform to the shape shown in FIG. 5c. The particular manner in which the flexible members 32 are caused to flex upwardly or downwardly could be accomplished by allowing the conduits 36 to be angularly adjustable. That is, the conduits 36 could be angled upwardly to cause the flexible members 32 to flex upwardly or the user could select to angle the conduits 36 downwardly to cause the flexible members 32 to flex downwardly.

As is shown in FIG. 1, reference numerals 22 or other indicia are printed around each adjustment knob 20. Since the present invention viewing assembly 10 can be selectively adjusted across a wide range of configurations, a chart or similar structural device may be provided that indicates to a person where to set the various adjustment knobs 20 in order to obtain a desired correction in the reflected surface 12. As such, a person need only turn the adjustment knobs 20 to a position that corresponds to their eyeglass lens prescription in order to optically correct the reflective surface 12 to their individual needs.

In the shown embodiment of FIGS. 2–5c, the flexible members 32 were preset at a generally convex curvature making it easy to create convex deformations in the flexible body 28 and the reflective surface 12. However, it will be understood that flexible members 32 that initially follow a concave curvature can also be disposed within the flexible body 28, thereby increasing the range of concave deformations that can be selectively created in the flexible body 28 and reflector surface 12.

While in the present embodiment, it is preferred that the shape of the flexible body 28 be controlled by the flexible members 32 and adjustment knobs 20, it is understood by those skilled in the art that other methods could be used to control the shape of the flexible body 28. For instance, the flexible body 28 could be surrounded by a contractible ring (not shown) or retractable fingers (not shown) could extend inwardly from the frame 30 for supplying pressure to the circumference of the flexible body 28. Similarly, the present invention is not limited to the use of manually adjustable knobs 20. The position of the flexible members 32 can be automatically controlled. For instance, the tensioning mechanisms 34 could be coupled to stepper motors (not shown) which are controlled by a microprocessor (not shown) which can actuate the stepper motors and tensioning mechanisms 34 to a position which corresponds to a particular prescription input into a key pad or other input mechanism (not shown). Further, an infrared or other autofocusing system (not shown), once the particular prescription was input into the microprocessor, could automatically adjust the focal length of the reflective surface 12.

Figure 6:
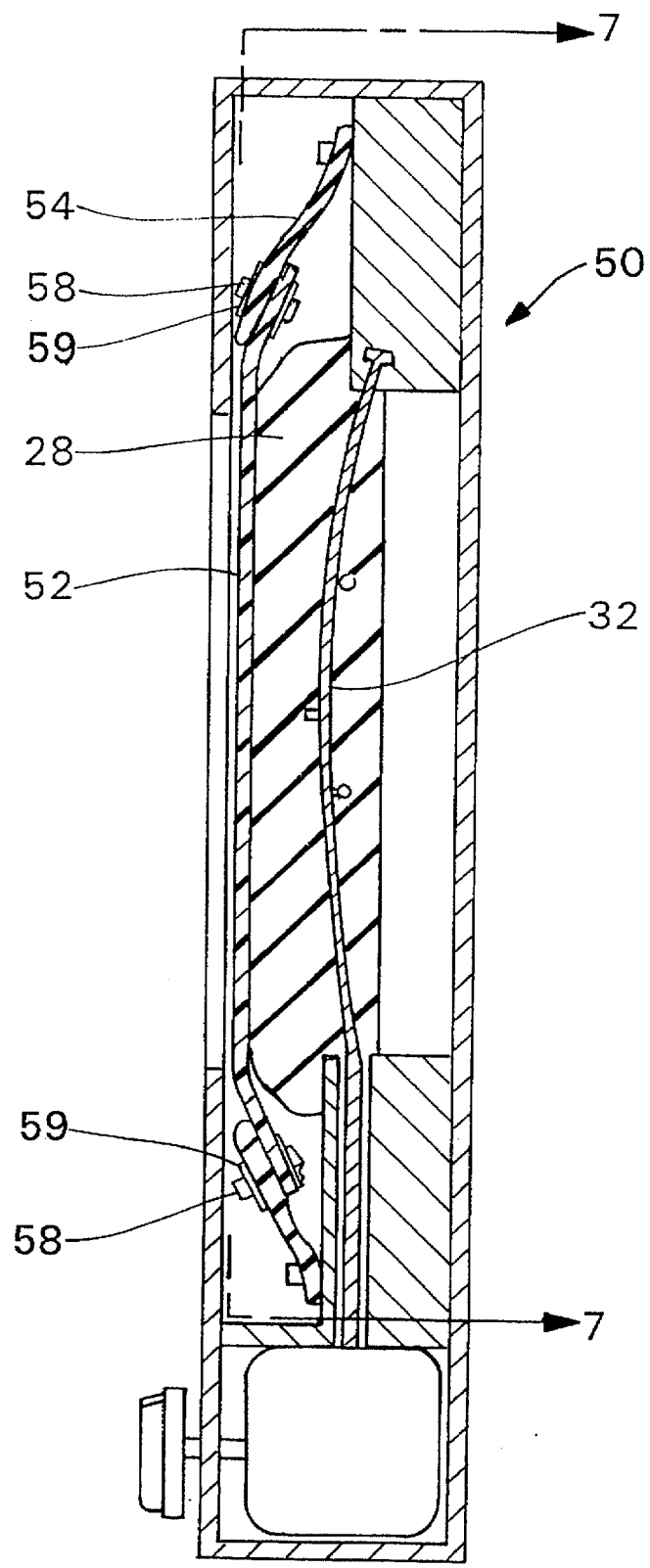
FIG. 6 is a cross-sectional view of an alternate embodiment of the present invention viewing assembly.
Figure 7:
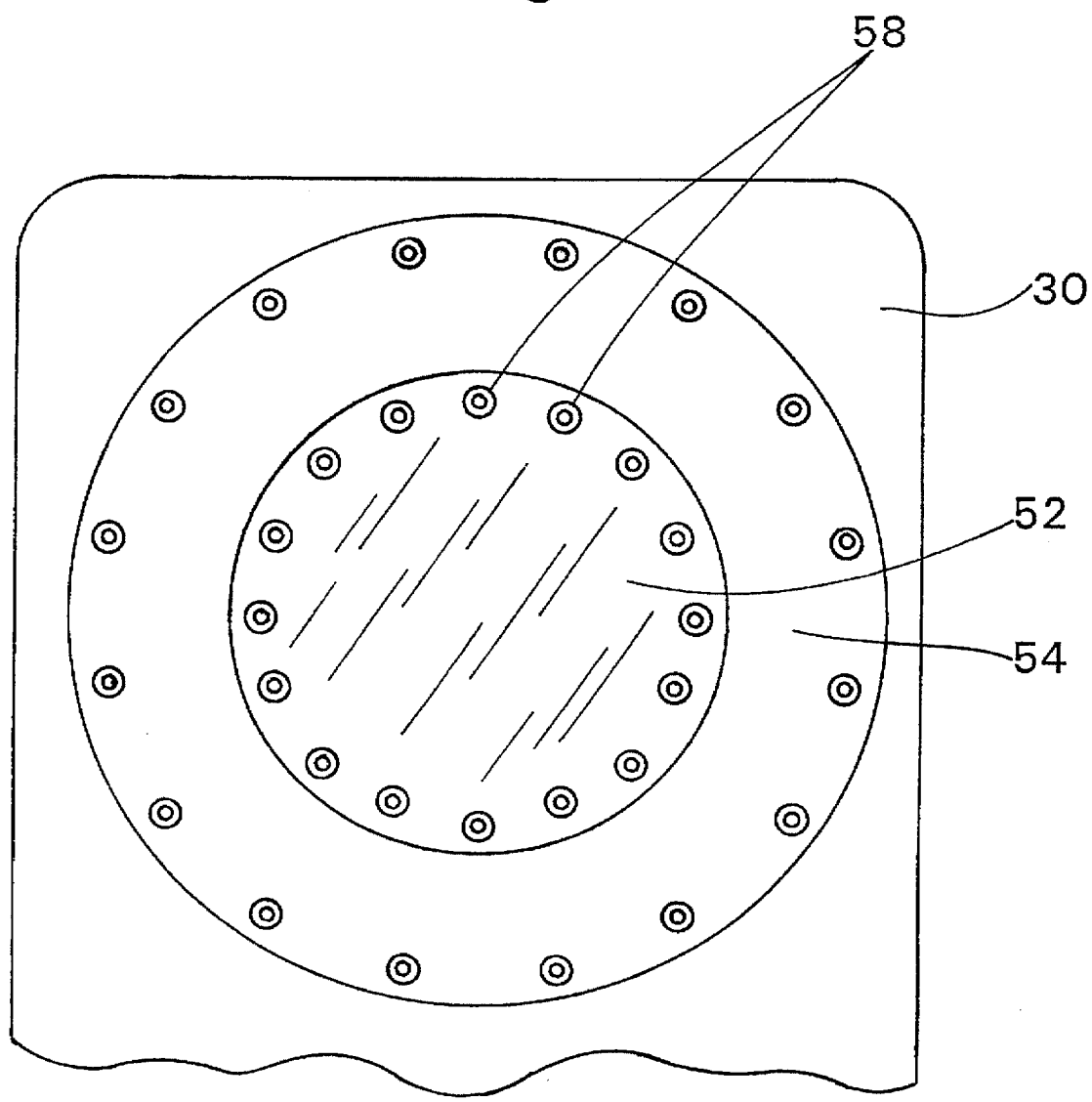
FIG. 7 is a forward view of the alternate embodiment of FIG. 6, viewed along section line 7—7.

Referring to FIG. 6, an alternative embodiment of the present invention viewing assembly 50 is shown. In this embodiment, the reflective surface 52 is not formed upon the flexible body 28, as has been previously described, but is biased against the flexible body 28. The flexible body 28 is deformed by the manipulation of the flexible members 32 that travel through the flexible body 28, as has been previously described. Referring to FIG. 7 in conjunction with FIG. 6, it can be seen that the reflective surface 52 is a sheet of reflective material, such as MYLAR®, pulled taut around its periphery by an elastic ring 54. The elastic ring 54, in turn, is attached to the rigid frame structure 30 that surrounds the flexible body 28. The reflective surface 52 is attached to the elastic ring 54 with a plurality of mechanical fasteners 58 that are symmetrically disposed around the periphery of the reflective surface 52. Each mechanical fastener 58 may include plastic washers 59 to help interconnect the reflective surface 52 to the elastic ring 54 by expanding the area of contact between each component. However, it will be understood that the reflective surface 52 can be attached to the elastic ring 54 in any manner, such as through the use of adhesives or by sewing the two components together along a seam. The elastic ring 54 is preferably constructed of latex sheet rubber or gum sheet rubber with a thickness in the range of $\frac{1}{32}$ to $\frac{1}{16}$ inches. The elastic ring 54 can be attached to the rigid frame structure 30 utilizing any known means of attachment. The elastic ring 54 is stretched between the reflective surface 52 and the rigid frame support 30. Consequently, the elastic ring 54 biases the reflective surface 52 against the flexible body 28 and the reflective surface 52 is held taut against the flexible body 28 without wrinkles or creases.

Since the reflective surface 52 is held taut against the flexible body 28, the reflective surface 52 conforms to the flexible body 28 such that any deformations in the flexible body 28 are transferred to the reflective surface 52. As such, by selectively creating spherical and/or cylindrical shape adjustments in the flexible body 28, the reflective surface 52 can be shaped along any desired toric curvature, thereby creating an optical correction as desired. Spherical and/or cylindrical changes in the shape of the flexible body 28 are created by selectively applying tension and compression forces to the flexible body 28, as has been previously described.

Figure 8:
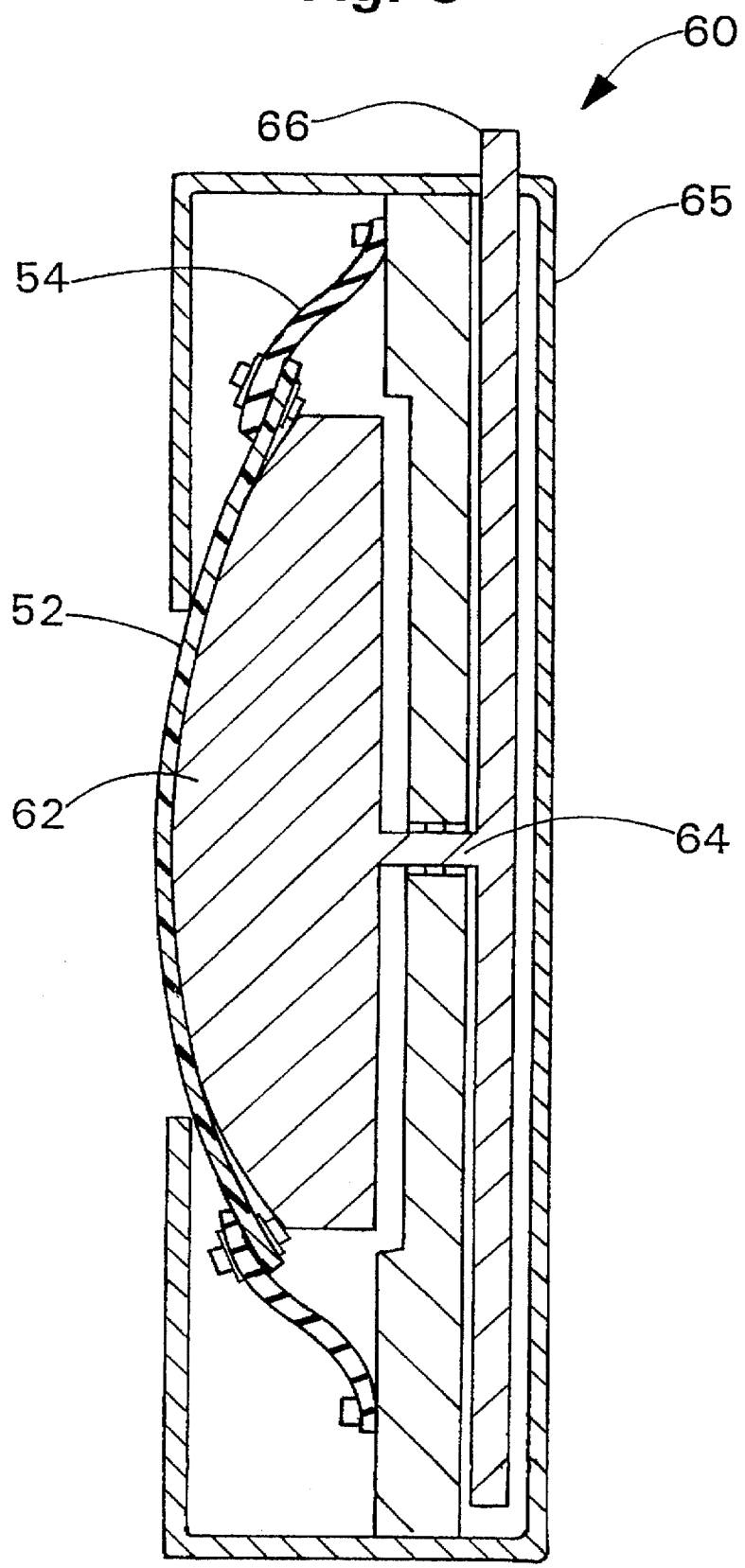
FIG. 8 is a cross-sectional view of a third embodiment of the present invention viewing assembly.

Referring to FIG. 8, there is shown a third embodiment of the present invention viewing assembly 60, wherein the adjustable flexible body 28 shown previously in the embodiment of FIG. 6 is replaced by a shaped static structure 62. In the shown embodiment, the reflective surface 52 is pulled taut over the static structure 62 by the elastic ring 54, whereby the reflective surface 52 conforms to the shape of the static structure 62. The static structure 62 can be made into any desired shape. As a result, the static structure 62 can be custom made to correct the vision deficiencies of a specific person. For example, if a person has a specific eyeglass prescription, a static structure 62 can be fabricated to match that prescription. The static structure 62 would thereby create a specific curvature in the reflective surface 52 that would optically correct a reflected image as needed. However, creating a static structure 62 for a specific person's optical requirements does not lend itself to mass production. As such, in a preferred embodiment, the static structure 62 is manufactured with a common toric curvature. Consequently, the reflective surface 52 is deformed to the toric curvature of the static structure 62, creating a corresponding corrected reflected image.

It will be understood that a toric surface has a different radius of curvature along each meridian on the surface. As such, when a toric curvature is applied to a mirror, the reflected image changes if the mirror is rotated about its center. In the shown embodiment, the static structure 62 is attached to a shaft 64. The shaft 64 is connected to an adjustment wheel 66 that extends beyond the housing 65 of the viewing assembly 60. As such, by manually rotating the adjustment wheel 66, the static structure 62 is rotated about its midaxis, via the shaft 64. As the static structure 62 is rotated, changes in the orientation of the static structure 62 are transferred to the reflective surface 52. The image reflected by the reflective surface 52 therefore changes as the static structure 62 moves below the reflective surface 52 and the curvature of the reflective surface 52 changes. By creating a toric curvature on the static structure 62, and providing a means to rotate the static structure 62 about its midaxis, the reflective toric surface 52 can be selectively adjusted to correct a large range of common optical deficiencies.

Figure 9:
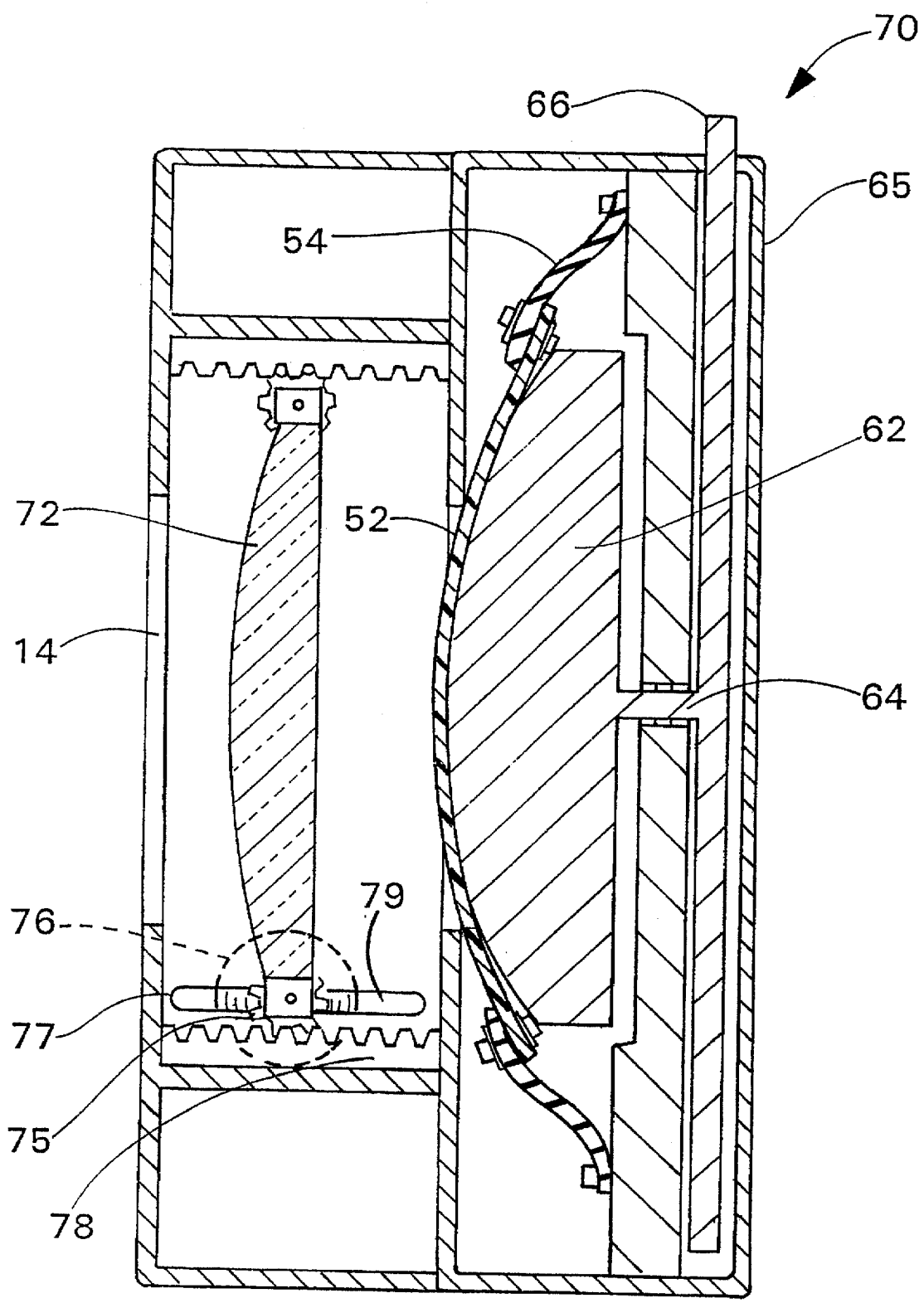
FIG. 9 is a cross-sectional view of a fourth embodiment of the present invention viewing assembly.

Referring to FIG. 9, there is shown a fourth embodiment of the present invention 70 wherein a corrective lens 72 is disposed in front of the reflective surface 52. The reflective surface 52 is held taut over a shaped static structure 62 by an elastic ring 54. As has been explained with previous embodiments, the reflective surface 52 therefore conforms to the shape of the static structure 62. In the shown embodiment, the static structure 62 is shaped to have a cylindrical curvature. As a result, the reflective surface 52 is also shaped to have a corresponding cylindrical curvature. The static structure 62 is coupled to be an adjustment wheel 66, via shaft 64. Consequently, as the adjustment wheel 66 is rotated, the static structure 62 rotates about its midaxis and curvature of the reflective surface 52 changes.

The corrective lens or optic element 72 is adjustably positioned in front of the reflective surface 52. The corrective lens 72 can be either convex or concave to produce spherical corrections in an image reflecting off the reflective surface 62 and passing through the corrective lens 72. The corrective lens 72 may also be of the fresnel type without departing from the spirit and scope of the invention. In the shown embodiment, a pinion gear 75 is rotatably attached to the corrective lens 72. A shaft 77 passes through the center of the pinion gear 75 and joins the pinion gear 75 to an adjustment knob 76 on the exterior of the viewing assembly 70. The shaft 77, connecting the adjustment knob 76 to the pinion gear 75, passes through a slotted opening 79 in the housing 65. The pinion gear 75 rides along rack 78 inside the mirror housing 65. As such, the position of the corrective lens 72 relative the reflective surface 52 can be selectively adjusted, within the mirror housing 65, by rotating the adjustment knob 76 and moving the corrective lens 72 back and forth across the gear rack 78. By moving the corrective lens 72 back and forth in front of the reflective surface 52, a large range of spherical corrections can be produced in a reflected image.

In the shown embodiment, a person would view a reflected image by looking through the view window 14 in the mirror housing 65. By looking through the view window 14, a person is able to see the portion of the reflective surface 52 that is pulled taut over the shaped static structure 62. The shaped static structure 62 produces a cylindrical curvature in the reflective surface 52. Consequently, the reflected image viewed from the reflective surface 52 is optically corrected according to the cylindrical curvature reproduced in the reflective surface 52. The cylindrically corrected reflective surface 52 is viewed through the corrective lens 72. The corrective lens 72 produces spherical corrections in the image reflected from the reflective surface 52. As a result, the reflected image is corrected both spherically, by the corrective lens 72, and cylindrically by the shape of the reflective surface 52.

As has been previously described, the cylindrical curvature of the reflective surface 52 can be selectively changed by rotating the static structure 62 below the reflective surface 52. Furthermore, the spherical corrections produced by the corrective lens 72 can be selectively altered by varying the position of the corrective lens 72 relative the reflective surface 52. The compound optical corrections that can be produced in the reflective toric image allow the viewing assembly 70 to be individually adjusted by the viewer to correct the reflected image as needed. In the shown embodiment, the corrective lens 72 creates spherical corrections in the viewed reflected image, while the static structure 62 creates cylindrical corrections in the reflective surface 52. However, it should be understood that the static structure 62 can be used to produce any desired corrections in the reflective surface 52. Similarly, the corrective lens 72 can be used to produce any desired secondary corrections in the reflected image. Consequently, any combination of optical corrections can be produced.

While the foregoing description of the various embodiments of the viewing assembly discusses cylindrical, spherical and toric surfaces, it is understood by those skilled in the art that the present invention is not limited to configuring the reflective surface to have any particular shape. For instance, the reflective surface could be configured to have an aspherical or parabolic surface. Similarly, the reflective surface could be configured to reflect a magnified image as well as a corrected image. Alternatively, a magnifying lens could be placed in front of the reflective surface to magnify the reflected image.

In view of the multitude of differing embodiments described above, it should appear obvious that a person skilled in the art could combine elements for each embodiment and produce a viewing assembly not specifically described herein. It should therefore be understood that the embodiments described herein are merely exemplary and that a person skilled in the art may make such variations and modifications without departing from the spirit and scope of the invention. All possible combinations of the features of the disclosed embodiments and other obvious variations and modifications regarding differing physical geometric proportions, materials or functionally equivalent components are intended to be included within the scope of the invention as defined in the appended claims.

We claim:

1. A viewing apparatus, comprising:

a formable body which is flexible throughout;

a plurality of flexible members disposed within said formable body, said plurality of flexible members extending through the formable body, each of said flexible members being configured to have a predetermined curvature within said formable body;

a force adjustment device applying a force to a selected number of said flexible members, thereby altering the predetermined curvature of the selected number of said flexible members and changing the shape of the formable body by flection; and a reflective surface coupled to said formable body, whereby said reflective surface changes in shape with said formable body and produces an optical correction in a reflected image viewed from said reflective surface.

2. The apparatus according to claim 1, wherein said reflective surface is disposed on said formable body in corresponding facing engagement therewith.

3. The apparatus according to claim 1, wherein said reflective surface is a sheet of flexible material pulled taut against said formable body.

4. The apparatus according to claim 3, further comprising:
an elastic member coupled to said sheet of flexible material, said elastic member pulling said sheet of flexible material taut over said formable body.

5. The apparatus according to claim 1, wherein each of said plurality of flexible members extend through said formable body along differently oriented paths such that a force can be applied to a selected number of said flexible members by said force adjustment device to alter the shape of the selected number of said flexible members and said formable body.

6. The apparatus according to claim 1, wherein said force adjustment device includes a separate controller for adjusting the force applied to each of said plurality of flexible members.

7. The apparatus according to claim 1 wherein the force adjustment device is mechanically linked to the flexible members and mechanically applies a force thereto.

8. The apparatus according to claim 1 wherein the plurality of flexible members include a first set of flexible members which follow a spherical curvature and a second set of flexible members which follow a cylindrical curvature, wherein applying a force to at least one flexible member from the first set and at least one flexible member from the second set provides a toric optical correction in the reflected image viewed from the reflective surface.

9. A viewing apparatus comprising:
a flexible material having a front surface and a back surface, said front surface being reflective;
a support structure having a first surface receiving said back surface of said flexible material in corresponding facing engagement, said first surface having a contour;
a tensioning device pulling said flexible material taut over said first surface of said support structure, wherein said flexible material conforms to the contour of said first surface; and
an adjustment mechanism selectively adjusting said contour of said first surface, thereby altering the shape to which said flexible material conforms and creating a desired optical correction in an image reflected from said flexible material.

10. The apparatus according to claim 9, wherein said flexible material has a peripheral edge and said tensioning device includes an elastic member coupled to said peripheral edge, whereby said elastic member biases said flexible material against said support structure and symmetrically pulls said flexible material taut over said support structure.

11. The apparatus according to claim 9, wherein said support structure is a body of formable material and said adjustment mechanism includes a plurality of members selectively stressing said formable body, thereby selectively altering the contour of said formable body.

12. The apparatus according to claim 9, wherein said support structure is a body of formable material having a plurality of flexible members disposed therein, wherein each of said plurality of flexible members follows a predetermined curvature within said formable body and said adjustment mechanism further includes a force adjustment device applying a force to a selected number of said flexible members, thereby altering the predetermined curvature of the selected number of said flexible members and causing changes in the contour of said body of formable material.

13. The apparatus according to claim 12 wherein the body of formable material is an elastomeric material.

14. A viewing apparatus comprising:
a flexible formable body constructed of an elastomeric material;
a plurality of flexible members disposed within said formable body, each of said flexible members being configured to have a predetermined curvature within said formable body;
a force adjustment device applying a force to a selected number of said flexible members, thereby altering the predetermined curvature of the selected number of said flexible members and changing the shape of the formable body; and
a reflective surface coupled to said formable body, whereby said reflective surface changes in shape with said formable body and produces an optical correction in a reflected image viewed from said reflective surface.

15. The apparatus according to claim 14, wherein said reflective surface is disposed on said formable body in corresponding facing engagement therewith.

16. The apparatus according to claim 14, wherein said reflective surface is a sheet of flexible material pulled taut against said formable body.

17. The apparatus according to claim 16, further comprising:
an elastic member coupled to said sheet of flexible material, said elastic member pulling said sheet of flexible material taut over said formable body.

18. The apparatus according to claim 14, wherein each of said plurality of flexible members extend through said formable body along differently oriented paths such that a force can be applied to a selected number of said flexible members by said force adjustment device to alter the shape of the selected number of said flexible members and said formable body.

19. The apparatus according to claim 14, wherein said force adjustment device includes a separate controller for adjusting the force applied to each of said plurality of flexible members.

20. A viewing apparatus comprising:
a flexible material having a front surface, a back surface and a periphery, said front surface being reflective;
a support structure having a first surface receiving said back surface of said flexible material in corresponding facing engagement, said first surface having a contour;
a tensioning device pulling said flexible material taut over said first surface of said support structure by pulling around the periphery of the flexible material, wherein said flexible material conforms to the contour of said first surface; and
an adjustment mechanism selectively adjusting said contour of said first surface, thereby altering the shape to which said flexible material conforms and creating a desired optical correction in an image reflected from said flexible material.

21. The apparatus according to claim 20, wherein said support structure is a body of formable material and said adjustment mechanism includes a plurality of members selectively stressing said formable body, thereby selectively altering the contour of said formable body.

22. The apparatus according to claim 20, wherein said support structure is a body of formable material having a plurality of flexible members disposed therein, wherein each of said plurality of flexible members follows a predetermined curvature within said formable body and said adjustment mechanism further includes a force adjustment device applying a force to a selected number of said flexible members, thereby altering the predetermined curvature of the selected number of said flexible members and causing changes in the contour of said body of formable material.

23. The apparatus according to claim 22 wherein the body of formable material is an elastomeric material.

* * * * *